United States Patent [19]

Ochiai et al.

[11] 4,008,246
[45] Feb. 15, 1977

[54] AMINOTHIAZOLE DERIVATIVES

[75] Inventors: Michihiko Ochiai, Suita; Akira Morimoto, Ikeda; Yoshihiro Matsushita, Nishinomiya; Taiiti Okada, Kyoto, all of Japan

[73] Assignee: Takeda Chemical Industries, Ltd., Osaka, Japan

[22] Filed: Aug. 8, 1975

[21] Appl. No.: 603,237

[30] Foreign Application Priority Data

Aug. 9, 1974 Japan .................. 49-91810

[52] U.S. Cl. .................. 260/306.8 R; 260/243 C; 424/246
[51] Int. Cl.[2] .................. C07D 277/48
[58] Field of Search .................. 260/306.8 R

[56] References Cited

UNITED STATES PATENTS 2,829,084  4/1958  O'Neill et al. .............. 260/306.8 R
3,705,153  12/1972  Kaneko et al. .............. 260/306.8 R Primary Examiner—Richard J. Gallagher
Attorney, Agent, or Firm—Wenderoth, Lind & Ponack

[57] ABSTRACT

A compound of the formula:

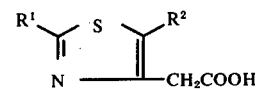

wherein $R^1$ stands for a halogenoethoxycarbonylamino and $R^2$ stands for hydrogen or a halogen, is an important intermediate for producing a cephalosporin derivative of the formula:

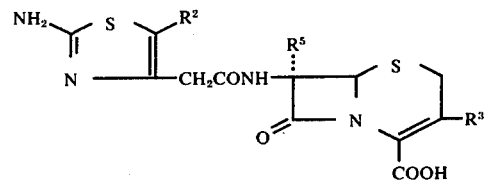

wherein $R^3$ stands for methyl, acetoxymethyl, carbamoyloxymethyl, an alkoxymethyl, an alkylthiomethyl, 2-carboxy-1-ethenyl, or a heterocyclic thiomethyl, $R^5$ stands for hydrogen or methoxy and $R^2$ has the same meaning as defined before, which is active against various pathogenic microorganisms even at a low concentration.

6 Claims, No Drawings

AMINOTHIAZOLE DERIVATIVES

This invention relates to novel compounds of the formula:

wherein $R^1$ stands for a halogenoethoxycarbonylamino and $R^2$ stands for hydrogen or a halogen.

After an intensive research we discovered that 2-(2'-halogenoethoxycarbonylamino)thiazol-4-ylacetic acid compounds (I'), which are of value as intermediates for the production of pharmaceutical products can be obtained, either by reacting an N-(2-halogenoethoxycarbonyl)thiourea, which is a novel compound, with an ω-halogenoacetoacetic acid or by reacting an 2-aminothiazol-4-ylacetic acid with a chloroformic acid 2-halogenoethyl ester and that a 2-(2'-halogenoethoxycarbonylamino)thiazol-4-ylacetic acid can be produced by hydrolyzing the resulting ester. The compounds (I') can be used for preparing, for example, novel 7-methoxycephalosporins of the formula;

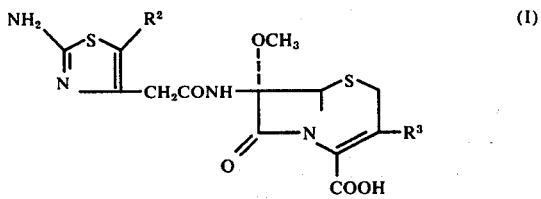

wherein $R^3$ stands for methyl, acetoxymethyl, carbamoyloxymethyl, an alkoxymethyl, an alkylthiomethyl, 2-carboxy-1-ethenyl, or a heterocyclic-thiomethyl group, or a pharmaceutically acceptable salt thereof and also relates to processes for producing the same.

Referring, now, to the above formula (I), $R^2$ means hydrogen or a halogen such as chlorine and bromine, $R^3$ stands for methyl, acetoxymethyl, carbamoyloxymethyl, an alkoxymethyl such as methoxymethyl, an alkylthiomethyl such as methylthiomethyl, 2-carboxy-1-ethenyl, or a heterocyclicthiomethyl group. The heterocyclic group contains not less than one nitrogen which may be in the oxide form or, in addition to nitrogen or nitrogens, such others as oxygen or/and sulfur. The nitrogen-containing heterocyclic group desirably has one to four hetero atoms in its heterocyclic ring and the ring may be 5 or 6 membered one. As such heterocyclic group are exemplified pyridyl, N-oxide-pyridyl, pyrimidyl, pyridazinyl, N-oxido-pyridazinyl, pyrazolyl, diazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl and so on. And these heterocyclic groups may have such common substituents as lower alkyl groups, e.g. methyl, ethyl, trifluoromethyl, propyl, isopropyl, butyl, and isobutyl, lower alkoxy groups, e.g. methoxy, ethoxy, propoxy, isopropoxy, and butoxy, halogens, e.g. chlorine, and bromine, and so on.

The 7-methoxycephalosporin compounds (I) may be used with the 4-carboxyl function being left free or, if desired, may be put to use as salts, for example the salts of nontoxic cations, e.g. sodium, potassium etc.; basic amino acids, e.g. arginine, ornithine, lysine, and histidine,; polyhydroxyalkylamine; e.g. N-methylglucamine, diethanolamine, triethanolamine, tris-hydroxymethylaminomethane and so on. The aforesaid compounds may each be used also with its 4-carboxyl group transformed into an ester, for example as a biologically active ester derivative which, for instance, is conducive to an increased blood level and a prolonged action. As the ester residues beneficial to this goal, there may be mentioned α-alkoxy-α-substituted methyl groups, e.g. alkoxylmethyl groups, α-alkoxyethyl groups such as methoxymethyl, ethoxymethyl, isopropoxymethyl, α-methoxyethyl, α-ethoxyethyl, etc.; alkylthiomethyl groups such as methylthiomethyl, ethylthiomethyl, isopropylthiomethyl, etc.; acyloxymethyl groups or α-acyloxy-α-substituted methyl groups such as pivaloyloxymethyl, α-acetoxybutyl, etc.

The contemplated 7-methoxycephalosporin compounds may take two tautomeric forms as shown below by way of formulas but, in this specification, the compound is shown in the thiazole form, i.e. formula (I),

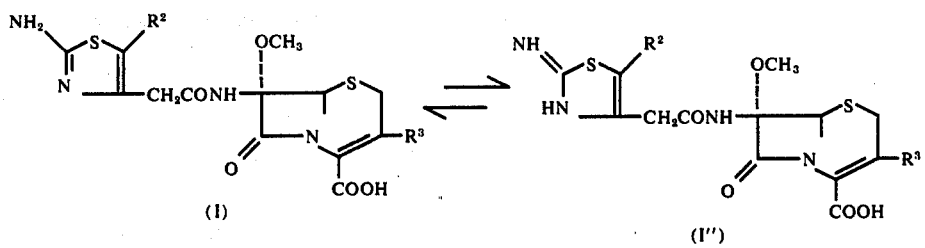

The 7-methoxycephalosporin compounds (I) each have a broad antimicrobial spectrum, i.e. activity against Gram-negative and Gram-positive bacteria, and particularly display greater activity than the known cephalosporins against antibiotic resistant strains of such Gram-negative bacteria as Escherichia coli, Serratia marcesens, Proteus vulgaris, Pseudomonas aeruginosa and so on. Therefore, these compounds are of use in the treatment of infections with the aforementioned bacteria in man and animals, giving excellent therapeutic effects. Like the known cephalosporin drugs, the contemplated compounds (I) may each be administered to patients in such dosage forms as injections, capsules, tablets, granules, etc. and, if necessary, together with a physiologically acceptable vehicle or excipient, as solutions, suspensions, solid preparations and so on.

Specifically, sodium 7α-methoxy-7β-(2-aminothiazol-4-ylacetamido)-3-(1-methyl-1H-tetrazol-5-ylthiomethyl)-3-cephem-4-carboxylate, for instance, is administered intramuscularly at a daily dose level of about 5 to 20 milligrams per kilogram body weight in three to five divided doses daily and this therapy is particularly effective in the treatment of respiratory and urinary tract infections.

The 7-methoxycephalosporin compounds (I) can be prepared by means of a method known for the production of analogous compounds thereof. For example, by reacting a 7-methoxycephalosporin compound of the formula:

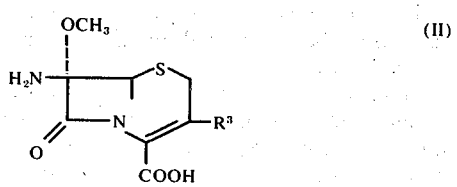

wherein the symbol has the meaning defined hereinbefore, with an aminothiazolylacetic acid derivative of the formula:

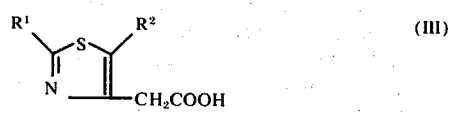

wherein $R^1$ stands for a protected amino group; $R^2$ has the meaning defined hereinabove, followed, if necessary, by removal of the protective group. The starting compound (II) for this reaction is put to use with its 4-carboxyl group being in the form of an alkali metal or organic amine salt, e.g. the sodium, potassium, triethylamine or other salt, or in the form of an ester which may be converted to a free carboxyl group under mild conditions, e.g. by the action of acid or alkali or by reduction. The ester may be exemplified by, for example, β-methylsulfonylethyl, trimethylsilyl, dimethylsilenyl, benzhydryl, β,β,β-trichloroethyl, phenacyl, p-methoxybenzyl, p-nitrobenzyl or methoxymethyl. $R^1$ in the mating material (III) means an amino group protected by an easily-removable amino-protective group which is used in general peptide chemistry, e.g. t-butoxycarbonyl, p-nitrobenzyloxycarbonyl, β,β,β-trichloroethoxycarbonyl, benzyloxycarbonyl, isobornyloxycarbonyl, etc. or by proton. The halogen atom, $R^2$, is normally chlorine or bromine, for instance. The reactive derivative of starting compound (III) may for example be the acid halide, acid anhydride, mixed acid anhydride, active amide or active ester. Normally this reaction can be conducted smoothly and with advantage in a solvent. The solvent is one which does not interfere with the reaction, e.g. acetone, tetrahydrofuran, dioxane, acetonitrile, chloroform, dichloromethane, dichloroethylene, pyridine, dimethylaniline, dimethylformamide, dimethylacetamide, dimethylsulfoxide or a mixture of such solvents. While there is no special limitation on the reaction temperature, the reaction is normally carried out under cooling or at room temperature. If necessary, the protective group is removed from the resultant 7-methoxycephalosporin derivative to produce a 7-methoxycephalosporin derivative of general formula (I). As to the removal of protective groups, t-butoxycarbonyl is removed by acid; β,β,β-trichloroethoxycarbonyl by reduction using zinc and acid; p-nitrobenzyloxycarbonyl by catalytic reduction; for instance. As to the removal of the ester residue from the 4-carboxyl group, benzhydryl, p-methoxybenzyl, etc. are removed by acid; β-methylsulfonylethyl by alkali; trimethylsilyl, dimethylsilenyl, etc. by water alone; β,β,β-trichloroethyl by reduction using zinc and acid; p-nitrobenzyl, etc. by reduction; for instance. The removal of these protective groups may be carried out simultaneously or, alternatively, one after another, which protective group should be first removed being determined in consideration of the types of protective groups, the subsequent reaction and other factors.

The 7-methoxycephalosporin compounds (I) wherein $R^2$ stands for hydrogen can be also prepared by reacting a compound of the formula:

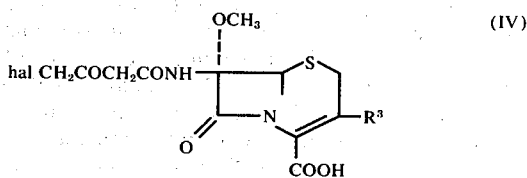

wherein hal stands for a halogen and $R^3$ has the meanings defined hereinbefore, with thiourea. The starting material compound (IV) can be obtained by the reaction of a 7-aminocephalosporin compound (II) with the 4-halogeno-3-oxobutyryl halide which is obtainable by the reaction of diketene with a halogen such as chlorine or bromine (Journal of the Chemical Society 97, 1987(1910)].

The 7-methoxycephalosporin compounds of formula (I) can be produced by reacting the above compound (IV) with thiourea. This reaction proceeds smoothly in a solvent, e.g. any of the common solvents which do not interfere with the contemplated reaction, e.g. water, methanol, ethanol, acetone, dioxane, acetonitrile, chloroform, ethylene chloride, tetrahydrofuran, ethyl acetate, dimethylformamide, dimethylacetamide or the like or a mixture of such solvents. While the addition of an acid acceptor is not essential, there are cases in which the reaction proceeds more smoothly in the presence of an acid acceptor, provided that the addition of the particular acceptor does not modify the cephalosporin nucleus. As the acceptor for this purpose, there may be mentioned inorganic and organic bases such as alkali metal hydroxides, alkali metal hydrogen carbonates, triethylamine, pyridine, N,N-dimethylaniline and so on. The starting compound (IV) is subjected to the reaction in the form of free acid, an alkali metal salt, e.g. sodium or potassium salt, or an ester such as those mentioned hereinbefore in connection with the 4-carboxyl group. Normally the reaction proceeds adequately at room temperature, although it may be conducted under heating or cooling as required.

The compounds (I) may be prepared by reacting a 7-methoxycephalosporin compound of the formula:

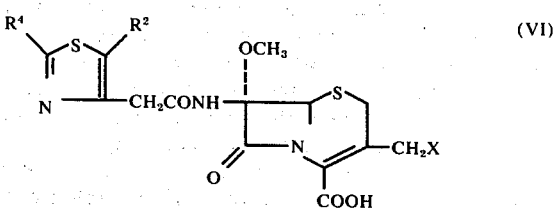

wherein X stands for an acetoxy or carbamoyloxy group; R⁴ stands for an amino group which may be protected; the other symbols have the meanings defined hereinbefore with a mercapto compound, followed, if necessary, by removal of the protective group. The compounds (VI) is normally used in the form of the sodium, potassium or other salt at the 4-carboxyl function.

The mercapto compound means, for example, any of such alkylmercaptans as methylmercaptan, ethylmercaptan, butylmercaptan, etc. or a heterocyclic compound containing a mercapto group. The term, heterocyclic compound, as used herein means a 5-membered or 6-membered cyclic compound containing, in addition to carbon, one or several heteroatoms such as N, O or/and S, and when N is involved, the N-oxides are also included. Thus, for example, imidazole, methylimidazole, pyrazole, triazole, methyltriazole, tetrazole, methyltetrazole, oxazole, isoxazole, thiazole, isothiazole, oxadiazole, thiadiazole, methylthiadiazole, pyridine-N-oxide, pyridazine-N-oxide, etc. fall within this category. Such a mercapto compound, though it may be used in its free form, is employed with advantage as an alkali metal salt, e.g. sodium or potassium salt. This reaction is preferably conducted in a solvent. For this purpose, use is made, for example, of water, heavy water or an organic solvent which is easily miscible with water and does not react with the material compounds, e.g. dimethylformamide, dimethylacetamide, dioxane, acetone, alcohol, acetonitrile, dimethylsulfoxide, tetrahydrofuran or the like. The reaction temperature and time depend upon the particular materials and solvent employed, among other factors but, generally, may be selected from the range of 0° C to 100 ° C and the range of a few hours to several days, respectively. The reaction is preferably carried out in the neighborhood of neutrality, i.e., at pH 2 to 8 and, for still better results, at pH 5 to 8. This reaction may at times be caused to proceed more smoothly by adding a quaternary ammonium salt having surface activity, e.g. trimethylbenzylammonium bromide, triethylbenzylammonium bromide, triethylbenzylammonium hydroxide or the like, to the reaction system. More satisfactory results may be achieved by conducting the reaction in an inert gaseous atmosphere, e.g., nitrogen gas, so as to prevent atmospheric oxidation of the mercapto compound.

The 7-methoxycephalosporin compounds (I) may be prepared also by reacting a 7-methoxycephalosporin compound of the formula:

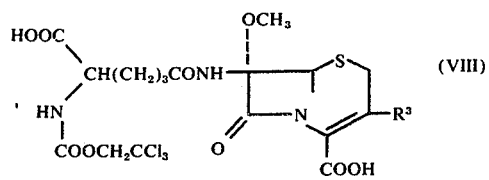

wherein the symbol has the meaning defined hereinbefore, with a reactive derivative of an aminothiazolylacetic acid derivative of the formula (III) in the presence of a silylating agent and, then, subjecting the reaction product to a reaction leading to removal of the protected aminoadipoyl group. The 4-carboxyl group of starting material compound (VIII) may be free or have been esterified as in the aforementioned case of compound (II) insofar as the particular ester is not detrimental to the contemplated reaction. This reaction comprises reacting a compound (VIII) with a reactive derivative of a compound (III) in a suitable solvent and in the presence of a silylating agent such as a tri-substituted silyl derivative of a electro-negatively substituted amide. The reaction can be smoothly conducted at a temperature of −20° C to 50° C, normally in the range of 15° C to 45° C. The solvent may for example be chloroform, dichloromethane, acetonitrile or dioxane.

The aforementioned negatively substituted tri-substituted silyl derivative is a compound which is synthesized by reacting a electro-negatively substituted amide or imide with a tri-substituted silyl halide. As said amide or imide, there may be mentioned succinimide, phthalimide, cyanoacetamide, trifluoroacetamide, trichloroacetamide and so on. Particularly useful for the contemplated reaction are N-trimethylsilyltrifluoroacetamide and N-trimethylsilylphthalimide. The resultant reaction product, as it occurs in the reaction mixture or after a suitable treatment such as concentration or isolation, is subjected to a reaction leading to removal of the protected aminoadipoyl group. This reaction is normally conducted under conditions similar to those used for removal of β,β,β-trichloroethoxycarbonyl. Thus, for example, it comprises the reaction with zinc and aqueous acetic acid or aqueous formic acid. The reaction can normally be accomplished satisfactorily at room temperature, the range of 10° to 40° C being useful.

The 7-methoxycephalosporin compounds (I) as obtained by the processes thus far described in detail can be purified by per se conventional procedures, e.g. column chromatography, extraction, precipitation, recrystallization and so on.

The aminothiazolylacetic acid derivatives (III) can be prepared by, for example, reacting a chloroformic acid 2-halogenoethyl ester with thiocyanate to obtain a 2-halogenoethoxycarbonyl isothiocyanate, reacting thus obtained compound with ammonia to obtain an N-(2-halogenoethoxycarbonyl)thiourea, reacting the compound with an ω-halogenoacetic acid alkyl ester to give a 2-(2'-halogenoethoxycarbonylamino)thiazol-4-ylacetic acid alkyl ester and hydrolyzing the alkyl ester to obtain a 2-(2'-halogenoethoxycarbonylamino)-thiazol-4-ylacetic acid. Alternatively, the 2-(2'-halogenoethoxycarbonylamino)thiazol-4-ylacetic acid may be prepared by reacting an 2-aminothiazol-4-ylacetic acid alkyl ester with a chloroformic acid 2-halogenoethyl ester and hydrolyzing thus obtained 2-(2'-halogenoethoxycarbonylamino)thiazol-4-ylacetic acid alkyl ester.

The following description pertains, in the first place, to the process comprising reacting an N-(2-halogenoethoxycarbonyl)thiourea with a ω-haloacetoacetic acid alkyl ester. One of the reactants, an N-(2-halogenoethoxycarbonyl)thiourea, is prepared by reacting a chloroformic acid 2-halogenoethyl ester with thiocyanate and adding ammonia to the resultant 2-halogenoethoxycarbonyl isothiocyanate. This compound is a novel compound which has never been described in the literature. The halogen, substituting the 2-position of the ethyl group of said chloroformic acid ethyl ester, may for example be chlorine, bromine or/and fluorine, and one to three such halogen atoms may be present as substituents. Thus, trichloro-, dibromo and other compounds are commonly employed. Thiocyanic acid, for the purposes of this reaction, may be used in its free form, although normally it is more conveniently reacted as one of the salts of alkali metals, e.g. sodium, potassium, etc., the salts of heavy metals, e.g. copper, lead, etc., the ammonium salt and so on. This reaction proceeds smoothly in a solvent. The solvent to be normally employed is preferably a nonprotonating solvent, such as, acetone, methyl ethyl ketone, tetrahydrofuran, dioxane, acetonitrile, ether, benzene or toluene. Advantageously the reaction is conducted at a low temperature so as to avoid undesirable side reactions. Normally the reaction can be conducted smoothly within the range of 5° C. to −20° C.

The 2-halogenoethoxycarbonyl isothiocyanate thus obtained is so reactive that it is normally not isolated but the reaction mixture as such is subjected to the next treatment, i.e. reaction with ammonia, to produce an N-(2-halogenoethoxycarbonyl)thiourea. This ammonia-addition reaction may be carried out by introducing ammonia into the reaction mixture obtained in the aforementioned production stage for 2-halogenoethoxycarbonyl isothiocyanate, but normally the metal halide or ammonium halide by-produced from a chloroformic acid 2-halogenoethyl ester and a thiocyanate salt is first separated by filtration and, then, ammonia is introduced into the filtrate. The ammonia may be added in gaseous state, or a solution of ammonia in a suitable solvent, e.g. methanol or ethanol, may be introduced. The reaction is preferably carried out at a low temperature, normally within the range of 5° C to −10° C.

The reaction of an ω-haloacetoacetic acid compound with an N-(2-trichloroethoxycarbonyl)thiourea to produce a 2-(2′-trichloroethoxycarbonylamino)thiazol-4-ylacetic acid is normally conducted with advantage in a solvent and in the presence of a base. The solvent just mentioned may be any solvent that is able to dissolve the two starting materials and, at the same time, will not interfere with the contemplated reaction. Thus, use may be made of alcohols such as methanol, ethanol, propanol, etc.; ketones such as acetone, methyl ethyl ketone, etc.; ethers, such as ether, tetrahydrofuran, dioxane, etc. and their mixtures, to name but a few. This reaction proceeds smoothly in the presence of a base. As the base, there may be mentioned organic tertiary bases such as pyridine, picoline, quinoline, isoquinoline, triethylamine, tributylamine, N-methylpiperidine, N-methylmorpholine, N,N-dimethylaniline, N,N-diethylaniline and so on. The reaction proceeds at room temperature but, there are cases where the reaction is hastened by heating. The heating temperature in the neighborhood of the boiling point of the solvent employed is normally advantageous. As to the mating starting material, i.e. an ω-haloacetoacetic acid alkyl ester, there may be employed methyl ω-chloroacetoacetate, ethyl ω-chloroacetoacetate, methyl ω-bromoacetoacetate, ethyl ω-bromoacetoacetate and other ω-halogenoacetoacetic acid alkyl esters.

The following description pertains to the process which comprises reacting an 2-aminothiazol-4-ylacetic acid alkyl ester with 2-trichloroethyl chloroformate to produce a 2-(2′-halogenoethoxycarbonylamino)-thiazol-4-ylacetic acid alkyl ester. This reaction is normally conducted smoothly in a solvent and in the presence of a base. The solvent may be any solvent that will not interfere with the contemplated reaction. Normally, use is made of a nonprotonating organic solvent such as, chloroform, dichloromethane, dichloroethylene, carbon tetrachloride, chlorobenzene, ether, tetrahydrofuran, dioxane, acetone or methyl ethyl ketone, or a mixture of such solvents. The base may be any base that is able to accept or combine with the hydrogen halide by-produced in the course of the reaction and that does not interfere with the reaction. Thus, normally, organic tertiary bases such as pyridine, picoline, quinoline, isoquinoline, triethylamine, tributylamine, N-methylpiperidine, N-methylmorpholine, N,N-dimethylaniline or N,N-diethylaniline, may be employed. While the reaction proceeds smoothly at room temperature, the reaction system may be cooled or heated as occasion requires.

The 2-(2′-halogenoethoxycarbonylamino)thiazol-4-ylacetic acid ester thus obtained is partially hydrolyzed to a 2-(2′-halogenoethoxycarbonylamino)thiazol-4-ylacetic acid. This hydrolysis reaction is carried out in a solvent and in the presence of a base. The solvent is preferably one that is able to dissolve both the starting material ester and the base. Thus, normally, a mixture of water and an organic solvent miscible with water, such as methanol, ethanol, acetone or the like, is employed. As the base, use is normally made of an inorganic strong base such as, sodium hydroxide, potassium hydroxide or barium hydroxide. This reaction is conducted with advantage at a temperature near room temperature so as to avoid occurence of undesirable side reactions.

The present invention is illustrated in further detail below with reference to examples, but it is to be understood that the examples are solely for the purpose of illustration and not to be construed as limitations of the invention, and that many variations may be resorted to without departing from the spirit and scope of the invention. In this specification, "g.", "mg.", "m$l$", "cm.", "ppm", and "Mc" are abbreviations of "gram", "milligram", "milliliter", "centimeter", "part per million", and "megacycle", respectively. Resins named "Amberlite" are products manufactured by Rohm & Haas Co. in U.S.A. All the temperatures are uncorrected and the percentages are all on the weight basis except specifically defined.

[I] Preparation of 2-(2′,2′,2′-trichloroethoxycarbonylamino)thiazol-4-ylacetic acid 1. In 250 ml of acetone was dissolved 25.2 g. of potassium thiocyanate and while the solution was cooled at −20° C, 50 g. of 2,2,2-trichloroethyl chloroformate was added dropwise. After the dropwise addition has been completed, the mixture was stirred at that temperature for 30 minutes. The precipitated potassium chloride was filtered off. To the filtrate was added 26 g. of 17% methanolic ammonia at −10° C. The mixture was stirred for 45 minutes, after which the solvent was distilled off. The syrupy residue was recrystallized from aqueous methanol to obtain 21.8 g. of N-(2,2,2-trichloroethoxycarbonyl)thiourea as colorless prisms melting at 189°–190° C. Elemental analysis, for $C_4H_5Cl_3N_2O_2S$:

Calculated C, 19.10; H, 2.00; N, 11.14 Found C, 19.22; H, 1.96; N, 11.50.

2. In 3 ml of ethanol was dissolved 500 mg. N-(2,2,2-trichloroethoxycarbonyl)thiourea, 416 mg. ethyl ω-bromoacetoacetate and 363 mg. N,N-dimethylaniline and the solution was stirred at room temperature for 24 hours. After the solvent was distilled off under reduced pressure, the residue was dissolved in chloroform and washed once with 10% hydrochloric acid and, then, three times with a saturated aqueous solution of sodium chloride. After drying over magnesium sulfate, the chloroform layer was concentrated and the oily residue was passed through a column of silica gel and eluted with a 1:1 mixture of benzene and chloroform. The above isolation-purification procedure provided 540 mg. of ethyl 2-(2′,2′,2′-trichloroethoxycarbonylamino)thiazol-4-ylacetate, melting point: 91°–92° C. Elemental analysis, for $C_{10}H_{11}Cl_3N_2O_4S$:

Calculated C, 33.21; H, 3.07; N,7.75 Found C, 33.38; H, 2.85; N,7.73.

3. In 3 ml of acetone were dissolved 500 mg. N-(2,2,2-trichloroethoxycarbonyl)thiourea, 328 mg. ethyl ω-chloroacetoacetate and 237 mg. pyridine and the solution was stirred at room temperature for 24 hours. Thereafter, the treatment similar to (2) above gave 502 mg. of ethyl 2-(2′, 2′,2′-trichloroethoxycarbonylamino)thiazol-4-ylacetate. This product was identical with the compound prepared according to the procedure described above (2).

4. In 100 ml of dichloromethane were dissolved 18.6 g. ethyl 2-aminothiazol-4-ylacetate and 11.1 g. triethylamine and, while the solution was cooled with ice, 23.3 g. of 2,2,2-trichloroethylchloroformate was added dropwise. After the dropwise addition had been completed, the mixture was stirred for 1 hour, at the end of which time 50 ml of water was added to the reaction mixture.

The organic layer was taken, washed twice with 10% hydrochloric acid and once with water, then washed once with 10% aqueous sodium hydrogen carbonate solution and twice with saturated aqueous sodium chloride solution. Then, after drying over magnesium sulfate, the magnesium sulfate was filtered off and the dichloromethane was removed by distillation. To the resultant oily residue was added 80 ml of ethanol and the precipitate was filtered off (unreacted ethyl 2-aminothiazol-4-ylacetate: 9.7 g.). The filtrate was concentrated and passed through a column of silica gel and eluted with a 1:1 mixture of chloroform and benzene. The above isolation-purification procedure provided 12.2 g. of ethyl 2-(2′,2′,2′-trichloroethoxycarbonylamino)thiazol-4-ylacetate. This product was identical with the compound prepared according to (2) above.

5. In a mixture of 50 ml water and 50 ml methanol were dissolved 5.9 g. of ethyl 2-(2′,2′,2′-trichloroethoxycarbonylamino)thiazol-4-ylacetate and 1.3 g. of sodium hydroxide and the solution was stirred at room temperature for 4 hours. A major portion of the methanol was distilled off under reduced pressure and the residue was washed with 20 ml ethyl acetate, made acidic with 10% hydrochloric acid and extracted twice with 50 ml portions of ether. The ether extract was washed with water, dried and concentrated. The procedure provided 3.1 g. of 2-(2′,2′,2′-trichloroethoxycarbonylamino)thiazol-4-ylacetic acid, melting point: 164°–164.5° C. Elemental analysis, for $C_8H_7Cl_3N_2O_4S$:

Calculated C, 28.81; H, 2.12; N, 8.40 Found C, 28.92; H, 2.20; N, 8.44.

[II] Preparation of 2-(β,β,β-trichloroethoxycarbonylamino)-5-chlorothiazol-4-ylacetyl chloride hydrochloride 1. To a suspension of 5 g. of 2-(β,β,β-trichloroethoxycarbonylamino)thiazol-4-ylacetic acid in 75 ml of chloroform, was added dropwise 14.9 ml of a 10% (weight per volume) chlorine solution in dichloromethane. In 5 minutes after the completion of the addition, the mixture became a complete solution and was stirred for further 15 minutes, followed by extracting three times with 50 ml each of a 5% aqueous solution of sodium hydrogencarbonate. The extracts were combined and acidified with diluted hydrochloric acid to precipitate 2-(β,β,β-trichloroethoxycarbonylamino)-5-chlorothiazol-4-ylacetic acid. The precipitates were collected by filtration and recrystallized from chloroform-ether to give 3.5 g. of pure compound as colorless crystals melting at 112.0° C. Elemental analysis, for $C_8H_6O_4H_2Cl_4S$ Calculated C, 26.10; H, 1.64; N,7.61 Found C, 25.96; H, 1.80; N,7.25.

2. To a suspension of 4.2 g. of 2-(β,β,β-trichloroethoxycarbonylamino)-5-chlorothiazol-4-ylacetic acid in 10 ml of dichloromethane, was added 2.38 g. of phosphorus pentachloride and the mixture was stirred for 30 minutes at room temperature to precipitate 2-(β,β,β-trichloroethoxycarbonylamino)-5-chlorothiazol-4-ylacetyl chloride hydrochloride. The precipitates were collected by filtration and washed with a small amount of dichloromethane. Yield 3.38 g. colorless powder. Melting point: 99.8° C. Elemental analysis; for $C_8H_5O_3N_2Cl_5S \cdot HCl$ Calculated C, 22.72; H, 1.43; H, 6.62 Found C, 23.44; H, 1.63; N, 6.77.

[III]. Preparation of 7-methoxycephalosporin derivatives

EXAMPLE 1

1. In 20 ml of dichloromethane was suspended 6.67 g. of 2-(β,β,β-trichloroethoxycarbonylamino)thiazol-4-ylacetic acid and, while the suspension was stirred under cooling with ice, 4.15 g. of finely crushed phosphorus pentachoride was added, whereupon the suspended acid was completely dissolved. Then, after an elapse of about 5 minutes, fresh crystalline substance separated. The mixture was stirred at room temperature for 1 hour, after which time the precipitates were collected by filtration and rinsed with petroleum ether. The procedure provided 6.59 g. (yield 84.8%) of 2-(β,β,β-trichloroethoxycarbonylamino)thiazol-4-ylacetyl chloride.hydrochloride, melting point: 109.7° C (decomposition). Elemental analysis, for $C_8H_6O_3N_2Cl_4S \cdot HCl$ Calculated C, 24.73; H, 1.81; N, 7.21 Found C, 24.40; H, 1.63; N, 6.94.

2. In 10 ml of dichloromethane was dissolved 1.638 g. of benzhydryl 7α-methoxy-7β-aminocephalosporanate and, while the solution was cooled with ice, 1.5 ml of pyridine and, immediately thereafter, 2.70 g. of 2-(β,β,β-trichloroethoxycarbonylamino)thiazol-4-ylacetylchloride.hydrochloride were added. The mixture was stirred for 15 minutes. It was further stirred at room temperature for 20 minutes, after which it was poured in ice-water and extracted with ethyl acetate. The ethyl acetate layer was washed with 0.5N hydrochloric acid, water, a 5% aqueous sodium hydrogen carbonate solution and a saturated aqueous sodium chloride solution in the order mentioned, followed by drying over magnesium sulfate. Thereafter, the ethyl acetate was distilled off to obtain an oily residue. The oil was purified by chromatography on silica gel. The above procedure provided 1.096 g. (yield 39.9%) of benzhydryl 7α-methoxy-7β-[2-(β,β,β-trichloroethoxycarbonylamino)thiazol-4-ylacetamido]cephalosporanate.

The infrared absorption spectrum (KBr) of this product shows an absorption of β-lactam at 1770 cm$^{-1}$. The nuclear magnetic resonance spectrum (60 Mc, in deuteriochloroform) of the product shows a singlet assignable to the 3-acetyl group at 1.98 ppm, a singlet due to 2-methylene protons at 3.33 ppm, a singlet due to 7α-methoxy at 3.34 ppm, a singlet assignable to the methylene protons of the thiazolylacetic acid moiety at 3.74 ppm, a singlet due to the methylene protons of trichloroethoxycarbonyl at 4.84 ppm, a quartet due to 3-methylene protons at 4.90 ppm, a singlet of the 6-hydrogen at 5.05 ppm, a singlet assignable to the 5-hydrogen of the thiazole ring at 6.57 ppm, a singlet assignable to the methine protons of benzhydryl at 6.85 ppm, and a singlet due to the phenyl protons of benzhydryl at 7.30 ppm.

3. In 25 ml. of 90% formic acid was dissolved 990 mg. of benzhydryl 7α-methoxy-7β[2-(β,β,β-trichloroethoxycarbonylamino)thiazol-4-ylacetamido]cephalosporanate and, after the addition of 860 mg. zinc dust under cooling with ice, the mixture was stirred for 1 hour. The reaction mixture was poured in a saturated aqueous solution of sodium chloride and extracted with ethyl acetate. The ethyl acetate layer was washed with water, a 5% aqueous sodium hydrogen carbonate solution and a saturated aqueous sodium chloride solution in the order mentioned, followed by drying over magnesium sulfate. Thereafter, the ethyl acetate was distilled off to obtain 472 mg. (yield 61.5%) of benzhydryl 7α-methoxy-7β-(2-aminothiazol-4-ylacetamido)cephalosporanate. The infrared absorption spectrum of this product shows an absorption of β-lactam at 1770 cm$^{-1}$.

The nuclear magnetic resonance spectrum (60 Mc, in deuteriochloroform) of this ester shows a singlet assignable to the 3-acetyl group at 2.00 ppm, a quartet due to 2-methylene protons at 3.36 ppm, a singlet due to 7-methoxy at 3.45 ppm, a singlet assignable to the methylene protons of thiazolyl acetic acid at 3.56 ppm, a quartet assignable to 2-methylene protons at 4.90 ppm, a singlet due to 6-hdyrogen at 5.08 ppm, a singlet assignable to the 5-hydrogen of the thiazole ring at 6.28 ppm, a singlet due to the methine protons of benzhydryl at 6.93 ppm and a singlet due to the phenyl nuclear protons of benzhydryl at 7.30 ppm.

4. Under cooling with ice and stirring, 335 mg. of benzhydryl 7α-methoxy-7β-(2-aminothiazol-4-ylacetamido)cephalosporanate was added to a mixture of 1.5 ml trifluoroacetic acid and 1.5 ml anisole and the mixture was stirred for 30 minutes. The reaction mixture was poured in 50 ml anhydrous ether and the resultant white precipitates were collected and rinsed with ether. The procedure provided crude 7α-methoxy-7β-(2-aminothiazol-4-ylacetamido)cephalosporanic acid trifluoroacetate (185 mg.). This product was dissolved in a 5% aqueous solution of sodium hydrogen carbonate and the solution was run onto a column of Amberlite XAD-2(trade name) and eluted with water. This purification procedure provided 131 mg. (50.8%) of sodium 7α-methoxy-7β-(2-aminothiazol-4-ylacetamido)-cephalosporanate trihydrate. Elemental analysis, for $C_{16}H_{17}O_7N_4S_2Na \cdot 3H_2O$ Calculated C, 37.06%; H, 4.47%; N, 10.80% Found C, 37.36%; H, 4.14%; N, 10.50%.

The nuclear resonance spectrum (100 Mc, in $D_2O$) of this product showed a singlet due to 3-acetyl at 2.26 ppm, a quartet assignable to 2-methylene protons at 3.52 ppm, a singlet assignable to 7-methoxy at 3.70 ppm, a singlet assignable to the methylene protons of thiazolylacetic acid function at 3.80 ppm, a quartet due to 3-methylene protons at 4.95 ppm, a singlet due to 6-hydrogen at 5.32 ppm and a singlet assignable to the 5-hydrogen of the thiazole ring at 6.70 ppm.

5. The following compounds were prepared by a similar manner as above Example; 7α-methoxy-7β-(2-aminothiazol-4-ylacetamido)-3-methoxymethyl-3-cephem-4-carboxylic acid, 7α-methoxy-7β-(2-aminothiazol-4-ylacetamido)-3-(2-carboxylethenyl)-3-cephem-4-carboxylic acid, 7α-methoxy-7β-(2-aminothiazol-4-ylacetamido)-3 -methylthiomethyl-3-cephem-4-carboxylic acid.

EXAMPLE 2

1. In 4 ml of water containing 208 mg. of sodium hydrogen carbonate, there were dissolved 431 mg. of 7α-methoxy-7β-(2-aminothiazol-4-ylacetamido)cephalosporanic acid trifluoroacetate, 108 mg. of 1-methyl-1H-tetrazole-5-thiol and 24.6 mg. of triethylbenzylammonium bromide, and the reaction mixture was stirred at 60° C. for 6 hours in an atomosphere of nitrogen gas. After cooling, the reaction mixture was passed through a column of Amberlite XAD-2(trade name) and eluted with water. The above purification procedure provided 158 mg. (36.8%) of sodium 7α-methoxy-7β-(2-aminothiazol-4 ylacetamido)-3-(1-methyl-1H-tetrazol-5-ylthiomethyl)-3-cephem-4-carboxylate. Elemental analysis, for $C_{16}H_{17}O_5N_8SNa \cdot H_2O$ Calculated C, 35.68; H, 3.55; N, 20.86 Found C, 35.56; H, 3.36; N, 19.83.

The infrared absorption spectrum (KBr) of this product showed an absorption of β-lactam at 1750 cm$^{-1}$. The nuclear magnetic resonance spectrum (100 Mc, in $D_2O$) of the same product showed a quartet assignable to 2-methylene protons at 3.60 ppm, a singlet due to 7α-methoxy at 3.65 ppm, a singlet due to the methylene protons of thiazolylacetic acid function at 3.77 ppm, a singlet assignable to tetrazolemethyl protons at 4.17 ppm, a quartet assignable to 3-methylene protons at 4.30 ppm, a singlet due to 6-hydrogen at 5.24 ppm and a singlet due to the 5-hydrogen of the thiazole ring at 6.67 ppm.

2. The same procedure as (1) in the absence of triethylbenzylammonium bromide also gave sodium 7α-methoxy-7β-(2-aminothiazol-4-ylacetamido)-3-(1-methyl-1H-tetrazol-5-ylthiomethyl)-3-cephem-4-carboxylate salt. This product was identical with the compound obtained in (1).

EXAMPLE 3

In 20 ml of dichloromethane was dissolved 2.62 g. of benzhydryl 7α-methoxy-7β-amino-3-(1-methyl-1H-tetrazol-5-ylthiomethyl)-3-cephem-4-carboxylate and, under cooling with ice, 3.0 ml of pyridine and, then, 3.88 g. of 2-(β,β,β-trichloroethoxycarbonylamino)-thiazol-4-ylacetyl chloride. hydrochloride were added. The mixture was stirred for 15 minutes and, then, at room temperature for 20 minutes. Thereafter, the reaction mixture was poured in ice-water and extracted with ethyl acetate. The ethyl acetate layer was washed with 0.5N hydrochloric acid, water and a saturated aqueous sodium chloride solution in the order mentioned, followed by drying over magnesium sulfate. The ethyl acetate was distilled off to obtain an oily residue. This oil was purified by chromatography on silica gel. The procedure provided 1.82 g. (43%) of benzhydryl 7α-methoxy-7β-[2-(β,β,β-trichloroethoxycarbonylamino)-thiazol-4-ylacetamido]-3-(1-methyl-1H-tetrazol-5-ylthiomethyl)-3-cephem-4-carboxylate. A 1.50 g. portion of this ester was dissolved in 40 ml of 90% formic acid and, under cooling with ice and stirring, 1.30 g. of zinc dust was added. The reaction mixture was thus stirred for 1 hour. The reaction product was poured in a saturated aqueous solution of sodium chloride and extracted with ethyl acetate. The ethyl acetate layer was washed with water and a saturated aqueous sodium chloride solution, followed by drying over magnesium sulfate. The ethyl acetate was distilled off to obtain 753 mg. (63.4%) of crude benzhydryl 7α-methoxy-7β-(2-aminothiazol-4-ylacetamido)-3-(1-methyl-1H-tetrazol-5-ylthiomethyl)-3-cephem-4-carboxylate.

A 700 mg. portion of this product was added to a mixture of 3.0 ml trifluoroacetic acid and 3.0 ml anisole and, under cooling with ice and stirring, the reaction was carried out under cooling with ice and stirring. The reaction mixture was poured in 100 ml of anhydrous ether and the resultant precipitates were collected by suction and rinsed with ether. The procedure provided 373 mg. of 7α-methoxy-7β-(2-aminothiazol-4-ylacetamido)-3-(1-methyl-1H-tetrazol-5-ylthiomethyl)-3-cephem-4-carboxylic acid.trifluoroacetate: This product was dissolved in a 5% aqueous solution of sodium hydrogen carbonate and passed through a column of Amberlite XAD-2 (trade name), followed by elution with water. The above purification procedure provided 303 mg. of sodium 7α-methoxy-7β-(2-aminothiazol-4-ylacetamido)-3-(1-methyl-1H-tetrazol-5-ylthiomethyl)-3-cephem-4-carboxylate.

This product was completely identical with the product obtained in Example 2.

EXAMPLE 4

In 2 ml of water containing 95 mg. of sodium hydrogen carbonate were dissolved 200 mg. of 7α-methoxy-7β-(2-aminothiazol-4-ylacetamido)cephalosporanic acid.trifluoroacetate and 59 mg. of 6-methylpyridazine-3-thiol 1-oxide, followed by the addition of 11 mg. triethylbenzylammonium bromide. The mixture was stirred in an atmosphere of nitrogen gas at 60° C for 6 hours. After cooling, the reaction mixture was passed through a column of Amberlite XAD-2(trade name), followed by elution with water. The above purification procedure provided 62 mg. (yield 31.6%) of 7α-methoxy-7β-(2-aminothiazol-4-ylacetamido)-3-(6-methylpyridazin-3-ylthiomethyl)-3-cephem-4-carboxylic acid 1-oxide sodium salt. Elemental analysis, for $C_{19}H_{19}O_6N_6S_3Na.4.5H_2O$ Calculated C, 36.36; H, 4.58; N, 13.39 Found C, 36.12; H, 3.96; N, 12.64.

The infrared absorption spectrum (KBr) of this product showed an absorption of β-lactam at 1760 cm$^{-1}$. The nuclear magnetic resonance spectrum (100 Mc, in $D_2O$) showed a singlet assignable to the methyl protons on the pyridazine ring at 2.61 ppm, a quartet due to 2-methylene protons, a singlet due to 7α-methoxy protons at 3.65 ppm, a singlet of the methylene protons of the thiazolylacetic acid function at 3.77 ppm, a singlet due to 6-hydrogen at 5.24 ppm, a singlet assignable to the 5-hydrogen of the thiazole ring at 6.67 ppm and a doublet assignable to pyridazine ring protons at 7.51 and 7.88 ppm, respectively.

EXAMPLE 5

In 10 ml of water containing 184 mg. of sodium hydrogen carbonate were dissolved 556 mg. of 7α-methoxy-7β-(2-aminothiazol-4-ylacetamido)cephalosporanic acid.trifluoroacetate, 185 mg. of 2-methyl-1,3,4-thiadiazole-5-thiol sodium salt and 30 mg. of triethylbenzylammonium chloride and the solution was stirred in nitrogen streams at 58° C for 6 hours. After cooling, the reaction mixture was passed through a column of Amberlite XAD-2 (trade name), elution being carried out with water. Upon this purification treatment, there was obtained 121 mg. (yield 22.5%) of sodium 7α-methoxy-7β-(2-aminothiazol-4-ylacetamido)-3-(2-methyl-1,3,4-thiadiazol-5-ylthiomethyl)-3-cephem-4-carboxylate.

EXAMPLE 6

In 20 ml of dichloromethane was dissolved 953 mg. of benzhydryl 7α-methoxy-7β-(D-5-trichloroethoxycarbonylamino5-benzhydryloxycarbonylvalerylamido)cephalosporanate, followed by the addition of 740.8 mg. of N-trimethylsilyltrifluoroacetamide and 1555.4 mg. of 2-(β,β,β-trichloroethoxycarbonylamino)thiazol-4-ylacetylchloride.hydrochloride. The mixture was heated at 41° C with stirring for 24 hours. After cooling, the reaction mixture was filtered to remove the insoluble matters and the filtrate was concentrated under reduced pressure. The residue, which was crude benzhydryl 7α-methoxy-7β-[(D-5-trichloroethoxycarbonylamino-5-benzhydryloxycarboxyvaleryl)-(2-β,β,β-trichloroethoxycarbonylaminothiazol-4-ylacetyl)amino]-cephalosporanate, was dissolved in 10 ml of 90% formic acid. After the addition of 4 g. of zinc dust, the solution was stirred at room temperature for 5 hours and, then, filtered. To the filtrate was added 5 ml of a saturated sodium chloride solution, followed by extraction with ethyl acetate. The ethyl acetate layer was washed with water and dried over magnesium sulfate. The ethyl acetate was then distilled off and the oily residue was purified by chromatography on silica gel. The procedure provided 197 mg. (32.4%) of benzhydryl 7α-methoxy-7β-(2-aminothiazol-4-ylacetamido)cephalosporanate. This product was identical with the product obtained in Example 1 (3).

EXAMPLE 7

In 20 ml of acetonitrile was dissolved benzhydryl 7α-methoxy-7β-(D-5-trichloroethoxycarbonylamino-5-benzhydryloxycarboxyvalerylamido)-3-carbamoyloxymethyl-3-cephem-4-carboxylate, followed by the addition of 876.3 mg. of N-trimethylsilyllphthalimide and 1555.4 mg. of 2-(β,β,β-trichloroethoxycarbonylamino)thiazol-4-ylacetyl chloride.hydrochloride. The mixture was stirred under heating at 41° C for 24 hours. After the reaction mixture was cooled, the insoluble matters were filtered off and the filtrate was concentrated under reduced pressure. The resultant residue, i.e. crude benzhydryl 7α-methoxy-7β-[(D-trichloroethoxycarbonylamino-5-benzhydryloxycarboxyvaleryl)-(2-trichloroethoxycarbonylaminothiazol-4-ylacetyl)amino]-3-carbamoyloxymethyl-3-cephem-4- carboxylate, was dissolved in 10 ml of 90% acetic acid. After the addition of 4 g. zinc dust, the solution was stirred at room temperature for 8 hours. It was then filtered and 10 ml of saturated aqueous sodium chloride solution was added to the filtrate. The mixture was extracted with ethyl acetate, washed with water and dried. The oily product from the ethyl acetate layer was then purified by chromatography on silica gel. The procedure provided 120 mg. of benzhydryl 7α-methoxy-7β-(2-aminothiazol-4-ylacetamido)-3-carbamoyloxymethyl-3-cephem-4-carboxylate. Under cooling with ice, the above product was added to a mixture of 0.75 ml trifluoroacetic acid and 0.75 ml anisole and the mixture was stirred for 30 minutes, followed by the addition of 50 ml anhydrous ether. The resultant precipitate was collected by suction, rinsed with ether and dissolved in a 5% aqueous solution of sodium hydrogen carbonate. The solution was passed through a column of Amberlite XAD-2 (trade name), elution being carried out with water. Upon this purification, there was obtained sodium 7α-methoxy-7β-(2-aminothiazol-4-ylacetamido)-3-carbamoyloxymethyl-3-cephem-4-carboxylate.

EXAMPLE 8

In 30 ml of chloroform was dissolved 2.05 g. of benzhydryl 7α-methoxy-7β-amino-3-desacetoxycephalosporanate and, under cooling with ice 3.0 ml of pyridine and, then, 3.88 g. of 2-(β,β,β,-trichloroethoxycarbonylamino)thiazol-4-ylacetyl chloride.hydrochloride were added. The mixture was stirred for 15 minutes. Then, at room temperature, the mixture was further stirred for 20 minutes. Then, it was poured in 20 ml of ice-water and extracted with ethyl acetate. The ethyl acetate layer was washed with 0.5N hydrochloride, water and saturated aqueous sodium chloride solution, followed by drying over magnesium sulfate. The ethyl acetate was distilled off to obtain an oily residue, which was purified by chromatography on silica gel. The procedure provided benzhydryl 7α-methoxy-7β-[2-(β,β,β-trichloroethoxycarbonylamino)thiazol-4-ylacetamido]-3-desacetoxycephalosporanate. This ester was dissolved in 40 ml of 90% formic acid and, under cooling with ice and stirring, 1.30 g. of zinc dust was added and the reaction was allowed to proceed for 1 hour. The reaction mixture was poured in 30 ml of a saturated aqueous sodium chloride solution and extracted with ethyl acetate. The ethyl acetate layer was washed with a saturated aqueous sodium chloride solution and dried over magnesium sulfate. The ethyl acetate was then distilled off to obtain crude benzhydryl 7α-methoxy-7β-(2-aminothiazol4-ylacetamido)-3-desacetoxycephalosporate. Under cooling with ice, this crude product was added to a mixture of 3.0 ml. trifluoroacetic acid and 3.0 ml anisole and the mixture was stirred for 30 minutes. To the reaction mixture was added 100 ml of anhydrous ether and the precipitates were collected by suction. The procedure provided crude 7α-methoxy-7β-(2-aminothiazol-4-ylacetamido)-3-desacetoxycephalosporanic acid.trifluoroacetate. This product was dissolved in a 3% aqueous solution of sodium hydrogen carbonate and passed through a column of Amberlite XAD-2 (trade name), elution being carried out with water. The procedure provided 256 mg. of sodium 7α-methoxy-7β-(2-aminothiazol-4-ylacetamido)-3-desacetoxycephalosporanate.

EXAMPLE 9

To 50 ml of dichloromethane was added 4.68 g. of benzhydryl 7α-methoxy-7β-aminocephalosporanate and, while the mixture was cooled at −40° C, 2.4 g. of N,N-dimethylaniline was added. Under vigorous stirring, 2.91 g. of 4-bromo-3-oxobutyryl bromide was added dropwise over a period of about 10 minutes, during which time the temperature of the reaction mixture rose from −40° C to −15° C. Thereafter, stirring was continued at −15° C to −10° C for 30 minutes. The reaction mixture was washed with water, dilute hydrochloric acid, water and saturated aqueous sodium chloride solution, followed by drying. The solvent was then distilled off to obtain an oily residue. This product, i.e. crude benzhydryl 7α-methoxy-7β-(4-bromo-3-oxobutyrylamido)-cephalosporanate, was dissolved in 50 ml of methanol and, following the addition of 0.91 g. thiourea, the reaction was conducted at room temperature with stirring for 2 hours. The methanol was distilled off under reduced pressure and the residue was washed with ethyl acetate and dissolved by the addition of 30 ml water. Then, a 5% aqueous solution of sodium hydrogen carbonate was added and the substance that separated out was extracted with ethyl acetate. The ethyl acetate layer was washed with saturated sodium chloride solution and dried. The ethyl acetate was then distilled off to obtain 2.43 g. of an oily residue. This product was identical with the benzhydryl 7α-methoxy-7β-(2-aminothiazol-4-ylacetamido)-cephalosporanate obtained in Example 1 (3).

EXAMPLE 10

To 30 ml of dimethylacetamide was added 5.24 g. of benzhydryl 7α-methoxy-7β-amino-3-(1-methyl-1H-tetrazol-5-ylthiomethyl)-3-cephem-4-carboxylate and, under cooling at −40° C, 2.91 g. of 4-bromo-3-oxobutyryl bromide was added over a period of about 10 minutes. During this period, the temperature of the reaction mixture rose from −40° C to −15° C. The mixture was further stirred between 15° C to −10° C for an additional hour, after which it was poured in 100 ml of ice-water. The mixture was adjusted to pH 8.0–8.5 with sodium hydrogen carbonate and extracted with ethyl acetate. The ethyl acetate layer was washed with water, dilute hydrochloric acid and a saturated aqueous sodium chloride solution in the order mentioned, followed by drying. The ethyl acetate was then distilled off under reduced pressure to obtain an oily residue. This product, i.e. benzhydryl 7α-methoxy-7β-(4-bromo-3-oxobutyrylamido)-3-(1-methyl-1H-tetrazol-5-ylthiomethyl)-3-cephem-4-carboxylate, was dissolved in 50 ml of methanol and, following the addition of 0.91 g. thiourea, the mixture was stirred at room temperature for 2 hours. The methanol was distilled off under reduced pressure and the residue was washed with ethyl acetate and dissolved in 30 ml of water. Following the addition of a 5% aqueous solution of sodium hydrogen carbonate, the substance that had separated was extracted with ethyl acetate. The ethyl acetate layer was washed with water and saturated aqueous sodium chloride solution, followed by drying. The ethyl acetate was distilled off under reduced pressure to obtain crude benzhydryl 7α-methoxy-7β-(2-aminothiazol-4-ylacetamido)-3-(1-methyl-1H-tetrazol-5-ylthiomethyl)-3-cephem-4-carbonate. Under cooling with ice and stirring, this product was added to a mixture of 35 ml trifluoroacetic acid and 35 ml anisole and the reaction was allowed to proceed for 30 minutes. Then, following the addition of 700 ml anhydrous ether, the precipitate was collected by suction and rinsed with ether. The procedure provided crude 7α-methoxy-7β-(2-aminothiazol-4-ylacetamido)-3-(1-methyl-1H-tetrazol-5-ylthiomethyl)-3-cephem-4-carboxylic acid.trifluoroacetate. This product was dissolved in a 3% aqueous solution of sodium hydrogen carbonate and the solution was passed through a column of Amberlite XAD-2 (trade mark), elution being carried out with water. The procedure provided 1.25 g. of sodium 7α-methoxy-7β-(2-aminothiazol-4-ylacetamido)-3-(1-methyl-1H-tetrazol-5-ylthiomethyl)-3-cephem-4-carboxylate. This product was identical with the product obtained in Example 2 (1).

EXAMPLE 11

1. To a solution of 1.638 g. of 7α-methoxy-7β-aminocephalosporanic acid benzhydrylester dissolved in 10 ml of dichloromethane, was added under ice-cooling 1.5 ml of pyridine and then 2.22 g. of 2-(β,β,β-trichloroethoxycarbonylamino)-5-chlorothiazol-4-ylacetyl chloride.hydrochloride and the mixture was stirred for 30 minutes at room temperature, followed by pouring into ice-water. The mixture was extracted with ethyl acetate. The ethyl acetate layer was washed with 0.5N-hydrochloric acid, a 5% aqueous solution of sodium hydrrogencarbonate and saturated aqueous solution of sodium chloride, in this order and dried with magnesium sulfate, followed by removal of ethyl acetate to give oily residue. The oily residue was purified by chromatography on silica gel to obtain 7α-methoxy-7β-[2-(β,β,β-trichloroethoxycarbonylamino)-5-chlorothiazol-4-ylacetamido]-cephalosporanic acid benzhydrylester. The nuclear magnetic resonance spectrum (60 Mc, in CDCl$_3$) showed a singlet assignable to 3-acetyl protons at 2.00 ppm, a singlet due to methoxy protons at 3.42 ppm and a singlet due to trichloroethyl protons at 4.86 ppm.

2. To a solution of 1000 mg. of the product obtained in above (1) dissolved in 25 ml of 90% formic acid, was added 860 mg. of zinc powder under ice-cooling and stirring, followed by keeping the mixture under same conditions for 1 hour. The reaction mixture was poured into a saturated aqueous solution of sodium chloride and the mixture was extracted with ethyl acetate. The ethyl acetate layer was washed with water and dried with magnesium sulfate and then subjected to the distillation of ethyl acetate to give 7α-methoxy-7β-(2-amino-5-chlorothiazol-4-ylacetamido)cephalosporanic acid benzhydrylester. The nuclear magnetic resonance spectrum (60 Mc, in CDCl$_3$) showed a singlet due to acetyl protons at 2.02 ppm, a singlet due to methoxy protons at 3.48 ppm, and a singlet due to 6-hydrogen at 5.18 ppm.

3. To a mixture of 1.5 ml of trifluoroacetic acid and 1.5 ml of anisole was added 350 mg. of 7α-methoxy-7β-(2-amino-5-chlorothiazol-4-ylacetamido)cephalosporanic acid benzhydrylester, and the resultant mixture was stirred for 20 minutes. The reaction mixture was poured into 50 ml of dry ether to give white precipitates which were collected by filtration and washed with ether to give crude trifluoroacetic acid salt of 7α-methoxy-7β-(2-amino-5-chlorothiazol-4-ylacetamido)cephalosporanic acid. The crude salt was dissolved in 5 ml of a 5% aqueous solution of sodium hydrogencarbonate and the resultant solution was passed through a column of Amberlite XAD-2 (trade name), followed by elution with water to obtain sodium 7α-methoxy-7β-(2-amino-5-chlorothiazol-4-ylacetamido)cephalosporanate as colorless powder. The nuclear magnetic resonance spectrum (100 Mc, in D$_2$O) showed a singlet due to acetyl protons at 2.25 ppm, a singlet due to methylene protons of thiazolylacetyl group at 3.70 ppm, and a singlet due to 6-hydrogen at 5.29 ppm.

What is claimed is:

1. A compound of the formula

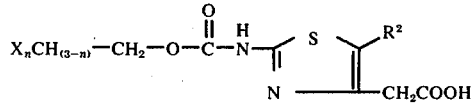

wherein X is chlorine or bromine,
  n is 1, 2 or 3, and
  $R^2$ is hydrogen, chlorine or bromine.

2. A compound according to claim 1 wherein $R^2$ is hydrogen.

3. A compound according to claim 1 wherein $R^2$ is chlorine or bromine.

4. A compound according to claim 1 wherein X is chlorine and n is 3.

5. A compound according to claim 1, said compound being, 2-(β,β,β-trichloroethoxycarbonylamino)thizol-4-ylacetic acid.

6. A compound according to claim 1, said compound being, 2-(β,β,β-trichloroethoxycarbonylamino)-5-chlorothiazol-4-ylacetic acid.

* * * * *